United States Patent [19]

Yale et al.

[11] 3,984,418
[45] Oct. 5, 1976

[54] HYDROGENATED DIELS-ALDER ADDUCTS OF BENZDIAZEPINES

[75] Inventors: Harry L. Yale, New Brunswick; James A. Bristol, Boonton, both of N.J.

[73] Assignee: E. R. Squibb & Sons, Inc., Princeton, N.J.

[22] Filed: Apr. 15, 1975

[21] Appl. No.: 568,358

[52] U.S. Cl............................ 260/293.55; 424/267
[51] Int. Cl.²...................................... C07D 471/04
[58] Field of Search................................ 260/293.55

[56] References Cited
UNITED STATES PATENTS

| | | | |
|---|---|---|---|
| 3,639,408 | 2/1972 | Nagata et al................. | 260/293.53 |
| 3,763,183 | 10/1973 | Carabateas.................... | 260/326.3 |
| 3,868,372 | 2/1975 | Hardtmann.................... | 260/251 A |

Primary Examiner—Henry R. Jiles
Assistant Examiner—C. Jaisle
Attorney, Agent, or Firm—Lawrence S. Levinson; Merle J. Smith; Donald J. Barrack

[57] ABSTRACT

Compounds having the structure

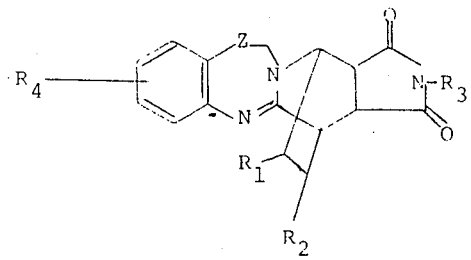

and the pharmaceutically acceptable salts thereof; wherein Z is oxygen, sulfur or methylene; $R_1$ is hydrogen, halogen, alkyl, aryl or arylalkyl; $R_2$ is hydrogen, alkyl, aryl, or arylalkyl; $R_3$ is hydrogen, alkyl, aryl or arylalkyl; and $R_4$ is hydrogen, halogen, alkyl, phenyl, dialkylamidosulfonyl or trifluoromethyl; have useful central nervous system activity.

8 Claims, No Drawings

HYDROGENATED DIELS-ALDER ADDUCTS OF BENZDIAZEPINES

SUMMARY OF THE INVENTION

Compounds having the structure

I

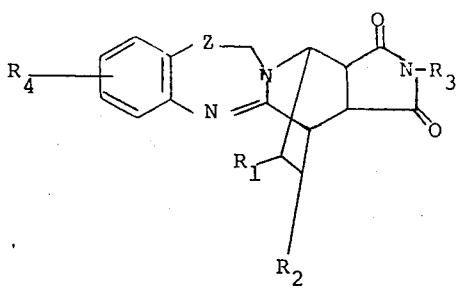

and the pharmaceutically acceptable salts thereof, have useful pharmacological activity. In formula I, and throughout the specification, the symbols are as defined below:

Z is oxygen, sulfur or methylene;
$R_1$ is hydrogen, halogen, alkyl, aryl or arylalkyl;
$R_2$ is hydrogen, alkyl, aryl or arylalkyl;
$R_3$ is hydrogen, alkyl, aryl or arylalkyl; and
$R_4$ is hydrogen, halogen, alkyl, phenyl, dialkylamidosulfonyl or trifluoromethyl;

with the proviso that when Z is oxygen or sulfur, and $R_4$ is phenyl or dialkylamidosulfonyl, $R_4$ must be para to the oxygen or sulfur atom.

The term "alkyl", as used throughout the specification, refers to straight or branched chain alkyl groups having 1 to 4 carbon atoms. Methyl is the preferred alkyl group.

The term "aryl", as used throughout the specification, refers to phenyl or phenyl substituted with halogen, alkyl or alkoxy. Phenyl is the preferred aryl group.

The term "halogen", as used throughout the specification, refers to chlorine, fluorine and bromine. Chlorine and bromine are the preferred halogens. The term "alkoxy", as used throughout the specification, refers to groups having the formula Y-O- wherein Y is alkyl as defined above. Methoxy is the preferred alkoxy group.

DETAILED DESCRIPTION OF THE INVENTION

The compounds of this invention have useful central nervous system stimulant activity in mammalian species, such as rats, dogs, etc., and can be used in the same manner as dextroamphetamine for the treatment of drowsiness or for the supression of appetite, or in the same manner as imipramine for the treatment of depression.

The compounds of this invention can be administered in a daily dose of from about 10 milligrams/70 kilograms to 2 grams/70 kilograms, preferably from about 25 milligrams/70 kilograms to 1 gram/70 kilograms. The compounds can be administered orally or parenterally in the form of tablets, capsules, elixirs, injectables or the like by incorporating the appropriate dosage of the compound with carriers according to accepted pharmaceutical practice.

The compounds of formula I can be prepared by selectively hydrogenating the double bond in the 14,15-position of compounds having the formula:

II

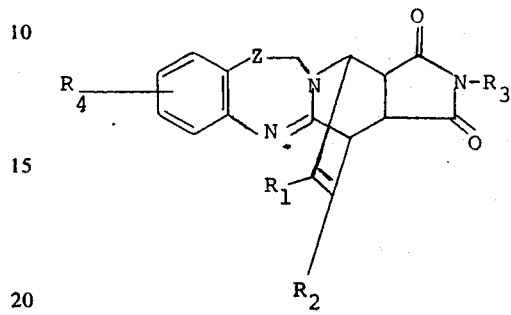

The selective hydrogenation can be carried out using gaseous hydrogen and Raney nickel as the catalyst. Reaction conditions are not critical but the hydrogenation will preferably be run at room temperature at a pressure of about 50 psig.

The compounds of formula II are set forth in United States patent application Ser. No. 531,512 filed Dec. 11, 1974. As disclosed therein, the compounds of formula II can be prepared from maleimides having the structure

III

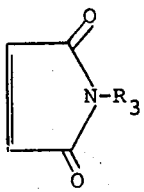

and from tricyclic compounds having the structure

IV

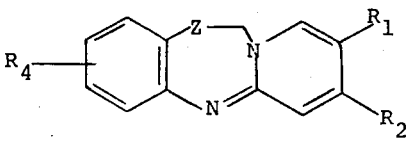

The N-maleimides of formula III are well known in the art and are readily obtainable by reaction of maleic anhydride and an amine having the formula $R_3$-$NH_2$. The compounds of formula IV are known: see, United States Pat. No. 3,825,549, issued July 23, 1974; United States patent application, Ser. No. 347,938, filed Apr. 4, 1973 now United States Pat. No. 3,857,850, issued Dec. 31, 1974; and United States application, Ser. No. 347,939, filed Apr. 4, 1973 now United States Pat. No. 3,856,801, issued Dec. 24, 1974.

The reaction of a tricyclic compound of formula IV with an N-substituted maleimide of formula III can be carried out in an organic solvent at elevated temperatures. While the choice of solvent and reaction conditions is not critical, the reaction will most preferably be run in an aromatic hydrocarbon solvent, such as xylene, under reflux conditions.

The compounds of formula I can be converted into pharmaceutically acceptable acid addition salts using procedures well known in the art. Illustrative acid addition salts are the hydrohalides, especially the hydrochloride and hydrobromide which are preferred, sulfate, nitrate, phosphate, tartrate, maleate, fumarate, citrate, succinate, methanesulfonate, toluenesulfonate, benzenesulfonate and the like.

The compounds of formula I wherein $R_1$ and $R_2$ are hydrogen are preferred.

The compounds of formula I wherein $R_1$, $R_2$ and $R_4$ are hydrogen are preferred.

The following examples are specific embodiments of this invention.

EXAMPLE 1

3a,4,13,13a-Tetrahydro-2-methyl-4,13-ethano-1H,6H-pyrrolo[3',4':4,5]pyrido[1,2-c][1,3,5]benzoxadiazepine-1,3(2H)-dione A mixture of 1.54g of 3a,4,13,13a-tetrahydro-2-methyl-4,13-etheno-1H,6H-pyrrolo[3',4':4,5-]pyrido[1,2c]-[1,3,5]benzoxadiazepine-1,3(2H)-dione in 150 ml of methanol is hydrogenated in a Parr vessel, using pyrophoric Raney nickel as a catalyst, until 0.005 mole of hydrogen is taken up. The mixture is filtered and the filtrate is concentrated in vacuo to give a solid. This is recrystallized from 40 ml of toluene to give 1.11g of the title compound, melting point 222°–224°C.

EXAMPLE 2

3a,4,10,11,13,13a-Hexahydro-2-methyl-4,13-ethano-1H-pyrrolo[3',4':4,5]pyrido[2,1-b][1,3]benzodiazepine-1,3(2H)-dione, hydrochloride (1:1)

A solution of 1.53g of 3a,4,10,11,13,13a-hexahydro-2-methyl-4,13-etheno-1H-pyrrolo[3',4':4,5-]pyrido[2,1-b][1,3]-benzodiazepine-1,3(2H)-dione in 100 ml of methanol is hydrogenated in a Parr vessel, using pyrophoric Raney nickel as a catalyst, until 0.005 mole of hydrogen is taken up. The mixture is filtered and concentrated to give a solid, which is dissolved in 20 ml of warm isopropanol. This solution is treated with an excess of a solution of hydrogen chloride in isopropanol, and the product that separates is recrystallized from 500 ml of isopropanol to yield 1.18g of the title compound, sintering at 320°C, melting point 344°–347°C.

EXAMPLES 3–29

Following the procedure of Example 1, but substituting the compound listed in column I for 3a,4,13,13a-tetrahydro-2-methyl-4,13-etheno-1H,6H-pyrrolo[3',-4':4,5]pyrido[1,2-c][1,3,5]benzoxadiazepine-1,3(2H)-dione, the compound listed in column II is obtained.

| Example | Column I | Column II |
|---|---|---|
| 3 | 3a,4,13,13a-tetrahydro-2-methyl-4,13-etheno-1H,6H-pyrrolo[3',4':4,5]pyrido[1,2-c][1,3,5]-benzothiadiazepine-1,3(2H)-dione | 3a,4,13,13a-tetrahydro-2-methyl-4,13-ethano-1H,6H-pyrrolo[3',4':4,5]pyrido[1,2-c][1,3,5]-benzothiadiazepine-1,3(2H)-dione |
| 4 | 10-chloro-3a,4,13,13a-tetrahydro-2-methyl-4,13-etheno-1H,6H,pyrrolo[3',4':4,5]pyrido-[1,2-c][1,3,5]benzoxadiazepine-1,3(2H)-dione | 10-chloro-3a,4,13,13a-tetrahydro-2-methyl-4,13-ethano-1H,6H-pyrrolo[3',4':4,5]pyrido-[1,2-c][1,3,5]benzoxadiazepine-1,3(2H)-dione |
| 5 | 3a,4,13,13a-tetrahydro-2-phenyl-4,13-etheno-1H,6H-pyrrolo[3',4':4,5]pyrido[1,2-c][1,3,5]-benzoxadiazepine-1,3(2H)-dione | 3a,4,13,13a-tetrahydro-2-phenyl-4,13-ethano-1H,6H-pyrrolo[3',4':4,5]pyrido[1,2-c][1,3,5]-benzoxadiazepine-1,3(2H)-dione |
| 6 | 3a,4,13,13a-tetrahydro-4,13-etheno-15-ethyl-8-trifluoromethyl-1H,6H-pyrrolo[3',4':4,5]-pyrido[1,2-c][1,3,5]benzothiadiazepine-1,3-(2H)-dione | 3a,4,13,13a-tetrahydro-4,13-ethano-15-ethyl-8-trifluoromethyl-1H,6H-pyrrolo[3',4':4,5]-pyrido[1,2-c][1,3,5]benzothiadiazepine-1,3-(2H)-dione |
| 7 | 9-t-butyl-14-chloro-2-(2-phenylethyl)-3a,4,13,-13a-tetrahydro-4,13-etheno-1H,6H-pyrrolo-[3',4':4,5]pyrido[1,2-c][1,3,5]benzothiadiazepine-1,3(2H)-dione | 9-t-butyl-14-chloro-2-(2-phenylethyl)-3a,4,13,-13a-tetrahydro-4,13-ethano-1H,6H-pyrrolo-[3',4':4,5]pyrido[1,2-c][1,3,5]benzothiadiazepine-1,3(2H)-dione |
| 8 | 11-methyl-2-n-propyl-3a,4,13,13a-tetrahydro-4,13-etheno-1H,6H-pyrrolo[3',4':4,5]pyrido-[1,2-c][1,3,5]benzothiadiazepine-1,3(2H)-dione | 11-methyl-2-n-propyl-3a,4,13,13a-tetrahydro-4,13-ethano-1H,6H-pyrrolo[3',4':4,5]pyrido-[1,2-c] [1,3,5]benzothiadiazepine-1,3(2H)-dione |
| 9 | 2-(4-chlorophenyl)-9-(dimethylamidosulfonyl)-14-(phenylmethyl)-3a,4,13,13a-tetrahydro-4,13-etheno-1H,6H-pyrrolo[3',4':4,5]pyrido[1,2-c]-[1,3,5]benzothiadiazepine-1,3(2H)-dione | 2-(4-chlorophenyl)-9-(dimethylamidosulfonyl)-14-(phenylmethyl)-3a,4,13,13a-tetrahydro-4,13-ethano-1H,6H-pyrrolo[3',4':4,5]pyrido[1,2-c]-[1,3,5]benzothiadiazepine-1,3(2H)-dione |
| 10 | 9-chloro-14-ethyl-2-(3-methylphenyl)-3a,4,13-13a-tetrahydro-4,13-etheno-1H,6H-pyrrolo[3',4':-4,5]pyrido[1,2-c][1,3,5]benzothiadiazepine-1,3-(2H)-dione | 9-chloro-14-ethyl-2-(3-methylphenyl)-3a,4,13-13a-tetrahydro-4,13-ethano-1H,6H-pyrrolo[3',4':-4,5]pyrido[1,2-c][1,3,5]benzothiadiazepine-1,3-(2H)-dione |
| 11 | 15-n-butyl-10-ethyl-2-isopropyl-3a,4,13,13a-tetrahydro-4,13-etheno-1H,6H-pyrrolo[3',4':-4,5]pyrido[1,2-c][1,3,5]benzothiadiazepine-1,3-(2H)-dione | 15-n-butyl-10-ethyl-2-isopropyl-3a,4,13,13a-tetrahydro-4,13-ethano-1H,6H-pyrrolo[3',4':-4,5]pyrido[1,2-c][1,3,5]benzothiadiazepine-1,3-(2H)-dione |
| 12 | 2-(3-t-butylphenyl)-9,14-diphenyl-3a,4,13,13a-tetrahydro-4,13-etheno-1H,6H,pyrrolo[3',4':-4,5]pyrido[1,2-c][1,3,5]benzothiadiazepine-1,3(2H)-dione | 2-(3-t-butylphenyl)-9,14-diphenyl-3a,4,13,13a-tetrahydro-4,13-ethano-1H,6H,pyrrolo[3',4':-4,5]pyrido[1,2-c][1,3,5]benzothiadiazepine-1,3(2H)-dione |
| 13 | 2-(2-bromophenyl)-15-phenyl-3a,4,13,13a-tetrahydro-4,13-etheno-1H,6H-pyrrolo[3',4':4,5]-pyrido[1,2-c][1,3,5]benzothiadiazepine-1,3-(2H)-dione | 2-(2-bromophenyl)-15-phenyl-3a,4,13,13a-tetrahydro-4,13-ethano-1H,6H-pyrrolo[3',4':4,5]-pyrido[1,2-c][1,3,5]benzothiadiazepine-1,3-(2H)-dione |
| 14 | 8,15-dichloro-2-phenyl-3a,4,10,11,13,13a-hexahydro-4,13-etheno-1H-pyrrolo[3',4':4,5]pyrido-[2,1-b][1,3]benzodiazepine-1,3(2H)-dione | 8,15-dichloro-2-phenyl-3a,4,10,11,13,13a-hexahydro-4,13-ethano-1H-pyrrolo[3',4':4,5]pyrido-[2,1-b][1,3]benzodiazepine-1,3(2H)-dione |
| 15 | 2,8,14-trimethyl-3a,4,10,11,13,13a-hexahydro-4,13-etheno-1H-pyrrolo[3',4':4,5]pyrido[2,-1-b][1,3]benzodiazepine-1,3(2H)-dione | 2,8,14-trimethyl-3a,4,10,11,13,13a-hexahydro-4,13-ethano-1H-pyrrolo[3',4':4,5]pyrido[2,-1-b][1,3]benzodiazepine-1,3(2H)-dione |
| 16 | 15-bromo-8-ethyl-2-(phenylmethyl)-3a,4,10,-11,13,13a-hexahydro-4,13-etheno-1H-pyrrolo- | 15-bromo-8-ethyl-2-(phenylmethyl)-3a,4,10,-11,13,13a-hexahydro-4,13-ethano-1H-pyrrolo- |

-continued

| Example | Column I | Column II |
|---|---|---|
| | [3′,4′:4,5]pyrido[2,1-b][1,3]benzodiazepine-1,3(2H)-dione | [3′,4′:4,5]pyrido[2,1-b][1,3]benzodiazepine-1,3(2H)-dione |
| 17 | 2-ethyl-14-phenylmethyl-3a,4,10,11,13,13a-hexahydro-4,13-etheno-1H-pyrrolo[3′,4′:4,5]-pyrido[2,1-b][1,3]benzodiazepine-1,3-(2H)-dione | 2-ethyl-14-phenylmethyl-3a,4,10,11,13,13a-hexahydro-4,13-ethano-1H-pyrrolo[3′,4′:4,5]-pyrido[2,1-b][1,3]benzodiazepine-1,3-(2H)-dione |
| 18 | 2-isopropyl-7-(diethylamidosulfonyl-14-phenyl-3a,4,10,11,13,13a-hexahydro-4,13-etheno-1H-pyrrolo[3′,4′:4,5]pyrido[2,1-b]-[1,3]benzodiazepine-1,3(2H)-dione | 2-isopropyl-7-(diethylamidosulfonyl-14-phenyl-3a,4,10,11,13,13a-hexahydro-4,13-ethano-1H-pyrrolo[3′,4′:4,5]pyrido[2,1-b]-[1,3]benzodiazepine-1,3(2H)-dione |
| 19 | 2-n-propyl-8-trifluoromethyl-3a,4,10,11,13,-13a-hexahydro-4,13-etheno-1H-pyrrolo[3′,4′:-4,5]pyrido[2,1-b][1,3]benzodiazepine-1,3-(2H)-dione | 2-n-propyl-8-trifluoromethyl-3a,4,10,11,13,-13a-hexahydro-4,13-ethano-1H-pyrrolo[3′,4′:-4,5]pyrido[2,1-b][1,3]benzodiazepine-1,3-(2H)-dione |
| 20 | 2,6-diphenyl-3a,4,10,11,13,13a-hexahydro-4,13-etheno-1H-pyrrolo[3′,4′:4,5]pyrido-[2,1-b][1,3]benzodiazepine-1,3(2H)-dione | 2,6-diphenyl-3a,4,10,11,13,13a-hexahydro-4,13-ethano-1H-pyrrolo[3′,4′:4,5]pyrido-[2,1-b][1,3]benzodiazepine-1,3(2H)-dione |
| 21 | 9-bromo-15-methyl-2-phenyl-3a,4,13,13a-tetrahydro-4,13-etheno-1H,6H-pyrrolo-[3′,4′:4,5]pyrido[1,2-c][1,3,5]benzoxadiazepine-1,3(2H)-dion | 9-bromo-15-methyl-2-phenyl-3a,4,13,13a-tetrahydro-4,13-ethano-1H,6H-pyrrolo-[3′,4′:4,5]pyrido[1,2-c][1,3,5]benzoxadiazepine-1,3(2H)-dione |
| 22 | 11-bromo-2,14-dimethyl-3a,4,13,13a-tetrahydro-4,13-etheno-1H,6H-pyrrolo[3′,4′:4,5]-pyrido[1,2-c][1,3,5]benzoxadiazepine-1,3-(2H)-dione | 11-bromo-2,14-dimethyl-3a,4,13,13a-tetrahydro-4,13-ethano-1H,6H-pyrrolo[3′,4′:4,5]-pyrido[1,2-c][1,3,5]benzoxadiazepine-1,3-(2H)-dione |
| 23 | 8-chloro-2-(phenylmethyl)-3a,4,13,13a-tetrahydro-4,13-etheno-1H,6H-pyrrolo[3′,4′:4,5]-pyrido[1,2-c][1,3,5]benzoxadiazepine-1,3-(2H)-dione | 8-chloro-2-(phenylmethyl)-3a,4,13,13a-tetrahydro-4,13-ethano-1H,6H-pyrrolo[3′,4′:4,5]-pyrido[1,2-c][1,3,5]benzoxadiazepine-1,3-(2H)-dione |
| 24 | 2-n-butyl-9-isobutyl-14-chloro-3a,4,13,13a-tetrahydro-4,13-etheno-1H,6H-pyrrolo[3′,4′:-4,5]pyrido[1,2-c][1,3,5]benzoxadiazepine-1,3(2H)-dione | 2-n-butyl-9-isobutyl-14-chloro-3a,4,13,13a-tetrahydro-4,13-ethano-1H,6H,-pyrrolo[3′,4′:-4,5]pyrido[1,2-c][1,3,5]benzoxadiazepine-1,3(2H)-dione |
| 25 | 2-isopropyl-14-methyl-9-phenyl-3a,4,13,13a-tetrahydro-4,13-etheno-1H,6H-pyrrolo[3′,4′:-4,5]pyrido[1,2-c][1,3,5]benzoxadiazepine-1,3(2H)-dione | 2-isopropyl-14-methyl-9-phenyl-3a,4,13,13a-tetrahydro-4,13-ethano-1H,6H-pyrrolo[3′,4′:-4,5]pyrido[1,2-c][1,3,5]benzoxadiazepine-1,3(2H)-dione |
| 26 | 2,15-dimethyl-9-trifluoromethyl-3a,4,13,13a-tetrahydro-4,13-etheno-1H,6H-pyrrolo[3′,4′:-4,5]pyrido[1,2-c][1,3,5]benzoxadiazepine-1,-3(2H)-dione | 2,15-dimethyl-9-trifluoromethyl-3a,4,13,13a-tetrahydro-4,13-ethano-1H,6H-pyrrolo[3′,4′:-4,5]pyrido[1,2-c][1,3,5]benzoxadiazepine-1,-3(2H)-dione |
| 27 | 9,14-diphenyl-2-(phenylmethyl)-3a,4,13,13a-tetrahydro-4,13-etheno-1H,6H-pyrrolo[3′,4′:-4,5]pyrido[1,2-c][1,3,5]benzoxadiazepine-1,3(2H)-dione | 9,14-diphenyl-2-(phenylmethyl)-3a,4,13,13a-tetrahydro-4,13-ethano-1H,6H-pyrrolo[3′,4′:-4,5]pyrido[1,2-c][1,3,5]benzoxadiazepine-1,3(2H)-dione |
| 28 | 9-(dimethylamidosulfonyl)-15-(phenylmethyl)-3a,4,13,13a-tetrahydro-4,13-etheno-1H,6H-pyrrolo[3′,4′:4,5]pyrido[1,2-c][1,3,5]benzodiazepine-1,3(2H)-dione | 9-(dimethylamidosulfonyl)-15-(phenylmethyl)-3a,4,13,13a-tetrahydro-4,13-ethano-1H,6H-pyrrolo[3′,4′:4,5]pyrido[1,2-c][1,3,5]benzodiazepine-1,3(2H)-dione |
| 29 | 2-isobutyl-3a,4,13,13a-tetrahydro-4,13-etheno-1H,6H-pyrrolo[3′,4′:4,5]pyrido[1,2-c][1,3,5]-benzoxadiazepine-1,3(2H)-dione | 2-isobutyl-3a,4,13,13a-tetrahydro-4,13-ethano-1H,6H-pyrrolo[3′,4′:4-4,5]pyrido[1,2-c][1,3,5]-benzoxadiazepine-1,3(2H)-dione |

What is claimed is:
1. A compound having the structure

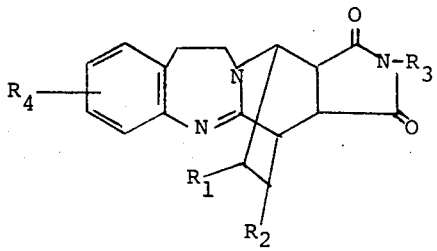

or a pharmaceutically acceptable salt thereof, wherein $R_1$ is hydrogen, halogen, alkyl, aryl or arylalkyl; $R_2$ is hydrogen, akyl, aryl or arylalkyl; $R_3$ is hydrogen, halogen, alkyl, aryl or arylalkyl; and $R_4$ is hydrogen, halogen, alkyl, phenyl, dialkylamidosulfonyl or trifluoromethyl; wherein aryl is phenyl or phenyl substituted with halogen, alkyl or alkoxy; and alkyl and alkoxy are groups having 1 to 4 carbon atoms.

2. A compound in accordance with claim 1 wherein $R_1$ and $R_2$ are hydrogen.

3. A compound in accordance with claim 1 wherein $R_3$ is hydrogen.

4. A compound in accordance with claim 1 wherein $R_3$ is alkyl.

5. A compound is accordance with claim 1 wherein $R_3$ is aryl.

6. A compound in accordance with claim 1 wherein $R_3$ is arylalkyl.

7. A compound in accordance with claim 1 wherein $R_4$ is hydrogen.

8. The compound in accordance with claim 1 having the name 3a,4,10,11,13,13a-hexahydro-2-methyl-4,-13-ethano-1H-pyrrolo[3′,4′:4,5]pyrido[2,1-b][1,3]benzodiazepine-1,3(2H)-dione, hydrochloride (1:1).

* * * * *